US00PP15285P3

(12) United States Plant Patent
Perkins

(10) Patent No.: US PP15,285 P2
(45) Date of Patent: Nov. 2, 2004

(54) ***ANGELONIA* PLANT NAMED 'CART PUR'**

(50) Latin Name: *Angelonia angustifolia*
Varietal Denomination: Cart Pur

(75) Inventor: Ralph Tyler Perkins, Gilroy, CA (US)

(73) Assignee: Goldsmith Seeds, Inc., Gilroy, CA (US)

( * ) Notice: Subject to any disclaimer, the term of this patent is extended or adjusted under 35 U.S.C. 154(b) by 96 days.

(21) Appl. No.: 10/397,990

(22) Filed: Mar. 25, 2003

(65) Prior Publication Data

US 2004/0194178 P1 Sep. 30, 2004

(51) Int. Cl.[7] ..... A01H 5/00
(52) U.S. Cl. ..... Plt./263
(58) Field of Search ..... Plt./263

*Primary Examiner*—Bruce R. Campell
*Assistant Examiner*—Michelle Kizilkaya
(74) *Attorney, Agent, or Firm*—Jondle & Associates P.C.

(57) ABSTRACT

An *Angelonia* cultivar particularly distinguished by purple color flowers with a white throat colored flowers, compact habit and good basal branching.

1 Drawing Sheet

Genus and species: *Angelonia angustifolia.*
Variety denomination: 'Cart Pur'.

BACKGROUND OF THE NEW PLANT

The present invention comprises a new and distinct cultivar of *Angelonia*, botanically known as *Angelonia angustifolia*, and hereinafter referred to by the cultivar name 'Cart Pur'. The new cultivar is asexually reproduced from vegetative cuttings and tissue culture resulting from the cross of the seed/pod parent 'AngelMist Purple Stripe', a purple and white bicolor commercial line that is unpatented× 'AngelMist Deep Plum', a deep purple that is a U.S. patented (U.S. Plant Pat. No. 12,040) line.

'Cart Pur' is a product of a planned breeding program intended to create new *Angelonia* plants with purple colored flowers with a white throat, compact habit, good basal branching and moderately vigorous growth.

The new cultivar was created in 2000 in Gilroy, Calif. and has been asexually reproduced repeatedly by vegetative cuttings and tissue culture in Gilroy, Calif., Andijk, The Netherlands, and Guatemala over a two and half-year period. The plant has also been trialed at Gilroy, Calif., Litchfield, Mich. and Andijk, The Netherlands. The present invention has been found to retain its distinctive characteristics through successive propagations; and this novelty is firmly fixed.

DESCRIPTION OF PHOTOGRAPH

This new *Angelonia* plant is illustrated by the accompanying photograph which shows blooms, buds, and foliage of the plant in full color, the colors shown being as true as can be reasonably obtained by conventional photographic procedures.

The Photograph shows the mature inflorescence.

DESCRIPTION OF THE NEW CULTIVAR

The following detailed descriptions set forth the distinctive characteristics of 'Cart Pur'. The data, which defines these characteristics, were collected from asexual reproductions carried out in Gilroy, Calif. The plant history and photograph were taken on 8 month old plants grown in one-gallon pots in fall/winter season, in a poly-covered greenhouse under 2–4 supplemental light and color readings were taken in the greenhouse in the winter season under natural light. Plants had been cut back prior to data readings taken. All major branches are cut back about 10–20 cm to keep the plant from becoming unruly. Color references are primarily to the R.H.S. Colour Chart of The Royal Horticultural Society of London (R.H.S.). Texture description details were observed under a dissecting microscope according to The New Royal Horticultural Society Dictionary of Gardening (1992).

THE PLANT

Classification:
*Botanical.*—*Angelonia angustifolia.*
*Commercial.*—Angelonia.
Form: Upright and erect.
Growth and branching habit: Good vigorous habit, well branched, pinching 1–2 times after transplant enhanced branching.
Height: From soil level to top of blooms: Approximately 50–60 cm.
Width: Approximately 30–40 cm including flowers.
Time to produce a finished flowering plant: 8–10 weeks for a 4–6 inch pot.
Outdoor plant performance: Full sun, free-flowering through the summer, some heat tolerance. Use in mixed container plantings, or mass planting in a bed.
Time to initiate roots: Approximately 18–23 days at warm temperatures.
Root description: Fibrous, free branching.

THE LEAVES

Arrangement: Opposite.
Length: 5.5–6.5 cm.
Width: 1.0–1.1 cm.
Leaf blade shape: Linear.
Leaf margin: Serrate.
Apex shape: Acute.
Base shape: Cuncate.

Mature leaf color: Upper side, RHS 137A (green) but a little darker; Underside, RHS 137C (green) with RHS 144C (yellow-green) mid-vein.
Juvenile leaf color: Upperside between RHS 143A & B; Underside, closest to RHS 144A, but greener.
Texture: Glandular hairs, physically leaving a sticky residue.
Venation: Pinnate.
Venation color: RHS3 144C (yellow-green).

THE STEM

Length: 50–60 cm from base of plant to tip of branch.
Diameter: 0.2–0.4 cm taken from the lower ⅓ of the stem.
Internodes length: 1.5–2.0 cm.
Branch aspect: 45–60 degree.
Color: Between RHS 144A and B (yellow-green).
Texture: Many glandular hair of various sizes, many with a yellow hue.
Stem anthocyanin: No.
Pedicel color: RHS 144A (yellow-green).
Pedicel length: 2.1–2.8 cm.
Pedicel diameter: 0.1 cm.
Pedicel texture: Many glandular hairs of various sizes, many with a yellow hue.
Pedicel anthocyanin: Some with a little at ovary end.
Pedicel aspect: 45–60 degrees.

THE BUD

Shape: Orbicular.
Diameter: 0.5–1.0 cm.
Length: 0.7–1.0 cm.
Color at tight bud: RHS 86C (violet) but a little greyer.

THE FLOWER

Blooming habit: Continuous throughout the growing season. Good floriferousness.
Floret and inflorescence type: Single, 2 lipped (5-petaled, fused at base) flowers, solitary in a leaf axis, on a terminal raceme.
Flower color, upper side, upper lip/lower lateral petals: RHS 83A (violet); Lateral petals: RHS 83A (violet); Mid-petals: RHS 83A (violet) base color with patch of RHS N155B (white) and RHS 145B (yellow-green), basally.
Flower color, underside: RHS 83B (violet) with larger patch of RHS N155B (white) on the lower midlobe basally.
Corolla color upper portion: RHS N155B (white) base color with small spots of RHS 83A (violet).
Corolla color lower portion: RHS 83B (violet) base color with small spots and bars of RHS 83A (violet).
Florets per raceme: 32–45.
Floret diameter: 2.3–2.4 cm.
Petal size, upper lip, 1 petal, and length: 0.8–0.9 cm from the corolla opening; width 0.6–0.7 cm.
Lower lip, lateral petal, and length: 0.9–1.0 cm from the corolla opening; width 0.8–0.9 cm.
Lower lip, mid-petal, length: 1.9–2.0 cm from ovary; width 0.8–0.9 cm.
Petal base: Fused.
Petal margin: Entire.
Petal texture: Papillose and short glandular hairs.
Sepals: 5, fused at base.
Sepal color: RHS 143A (green).
Sepal length: 0.4 cm.
Sepal width: 0.2 cm.
Sepal shape: Ovate.
Sepal apex: Acute.
Sepal anthocyanin: Yes.
Sepal texture: Many glandular hairs with a yellow hue.
Lastingness of individual blooms: 6–9 days.
Fragrance: None.

THE REPRODUCTIVE ORGANS

Stamens: 4, in pairs.
Filament color: RHS N155B (white).
Pollen color: RHS 201C (grey).
Pollen amount: Moderate.
Pistil: One.
Stigma color: RHS N155B (white).
Style color: RHS N155B (white).
Fruit seed set: Not observed.

DISEASE AND INSECT RESISTANCE

Not observed.

COMPARISON WITH KNOWN CULTIVARS

'Cart Pur' differs from the female parent, 'AngelMist Purple Stripe', in the following ways: 'Cart Pur' has a fuller and freer branching habit, and has purple colored flowers with a white throat and 'AngleMist Purple Stripe' has a white with purple striped flower.

'Cart Pur' differs from the male parent, 'AngelMist Deep Plum' in the following ways: 'Cart Pur' is more upright and has a fuller and freer branching habit, has superior vigor and has a purple color flowers with a white throat and 'AngelMist Deep Plum' has a deep purple flower.

I claim:

1. A new and distinct *Angelonia* plant as shown and described herein.

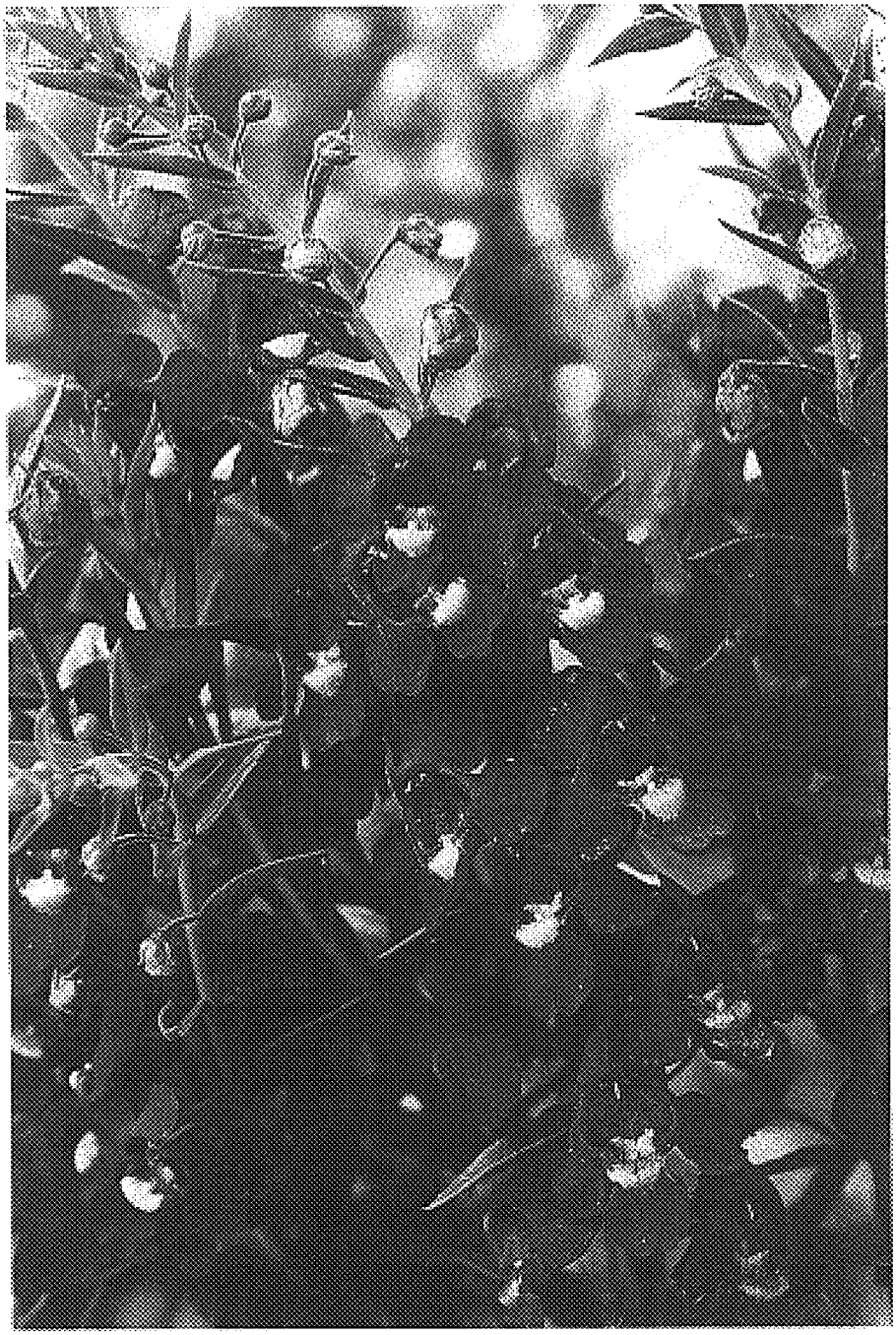

* * * * *